(12) United States Patent
Xia et al.

(10) Patent No.: US 10,012,077 B2
(45) Date of Patent: Jul. 3, 2018

(54) DOWNHOLE SENSOR FOR FORMATION FLUID PROPERTY MEASUREMENT

(71) Applicant: HALLIBURTON ENERGY SERVICES, INC., Houston, TX (US)

(72) Inventors: Hua Xia, Huffman, TX (US); Lizheng Zhang, Humble, TX (US); Robert Atkinson, Richmond, TX (US); Nestor Rodriguez, Shenandoah, TX (US); Christopher Michael Jones, Houston, TX (US); Darren Gascooke, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 172 days.

(21) Appl. No.: 14/895,032

(22) PCT Filed: Oct. 30, 2014

(86) PCT No.: PCT/US2014/063168
§ 371 (c)(1),
(2) Date: Dec. 1, 2015

(87) PCT Pub. No.: WO2016/068940
PCT Pub. Date: May 6, 2016

(65) Prior Publication Data
US 2016/0290133 A1    Oct. 6, 2016

(51) Int. Cl.
*E21B 49/08* (2006.01)
*E21B 47/01* (2012.01)
(Continued)

(52) U.S. Cl.
CPC ............ *E21B 49/081* (2013.01); *E21B 17/18* (2013.01); *E21B 47/011* (2013.01); *E21B 47/06* (2013.01);
(Continued)

(58) Field of Classification Search
CPC .. G01N 9/002; G01N 2009/006; G01N 11/16; G01F 1/8413; G01F 1/8409;
(Continued)

(56) References Cited

U.S. PATENT DOCUMENTS 2,635,462 A * 4/1953 Poole .................... G01N 9/002
310/25
3,618,360 A * 11/1971 Curtis .................... G01N 9/002
73/24.05
(Continued)

OTHER PUBLICATIONS

International Search Report and Written Opinion issued in related PCT Application No. PCT/US2014/063168, dated Jul. 24, 2015 (9 pages).
(Continued)

*Primary Examiner* — Kipp C Wallace
(74) *Attorney, Agent, or Firm* — Benjamin Fite; Baker Botts L.L.P.

(57) ABSTRACT

A downhole sensor package for detecting one or more thermophysical properties of a downhole fluid, comprising a sensor housing having a fluid input port and a fluid output port; an inner flow tube located within and axially defined with the sensor package housing; an outer flow annulus defined between the inner flow tube and the sensor housing, wherein the inner flow tube is in fluid communication with the outer flow annulus; and a vibration source and a vibration detector engaging the inner flow tube; and methods for using the same are disclosed.

20 Claims, 6 Drawing Sheets

(51) Int. Cl.
*E21B 17/18* (2006.01)
*E21B 47/06* (2012.01)
*G01V 1/48* (2006.01)
*G01V 1/52* (2006.01)

(52) U.S. Cl.
CPC .............. *E21B 47/065* (2013.01); *G01V 1/48* (2013.01); *G01V 1/52* (2013.01); *E21B 2049/085* (2013.01)

(58) Field of Classification Search
CPC .. G01F 1/849; G01F 1/8495; E21B 2049/085; E21B 49/10; G01H 3/00
See application file for complete search history.

(56) References Cited

U.S. PATENT DOCUMENTS

| | | | |
|---|---|---|---|
| 3,763,692 A * | 10/1973 | Agar | G01N 9/002 73/32 A |
| 4,524,610 A | 6/1985 | Fitzgerald et al. | |
| 6,029,501 A * | 2/2000 | Nishino | G01N 9/002 73/32 A |
| 7,036,363 B2 | 5/2006 | Yogeswaren | |
| 7,222,671 B2 * | 5/2007 | Caudwell | G01N 11/16 166/100 |
| 7,275,419 B2 | 10/2007 | Raffer | |
| 7,562,587 B2 | 7/2009 | Atkinson et al. | |
| 7,574,898 B2 | 8/2009 | Harrison et al. | |
| 7,784,330 B2 | 8/2010 | Angelescu et al. | |
| 7,874,199 B2 | 1/2011 | Chaudoreille et al. | |
| 2002/0178803 A1 | 12/2002 | Pelletier et al. | |
| 2003/0066652 A1 * | 4/2003 | Stegemeier | E21B 43/12 166/373 |
| 2009/0084178 A1 * | 4/2009 | Sinha | G01N 9/002 73/32 A |
| 2011/0042070 A1 * | 2/2011 | Hsu | E21B 47/102 166/250.01 |
| 2011/0083842 A1 * | 4/2011 | Indo | E21B 49/10 166/250.01 |
| 2012/0072128 A1 | 3/2012 | Gao | |
| 2013/0255368 A1 | 10/2013 | Harrison et al. | |
| 2015/0006084 A1 * | 1/2015 | Zuo | E21B 49/00 702/13 |
| 2017/0052098 A1 * | 2/2017 | Bell | G01N 9/002 |

OTHER PUBLICATIONS

International Preliminary Report on Patentability issued in related Application No. PCT/US2014/063168, dated May 11, 2017 (6 pages).

* cited by examiner

Signal excitation for density

Fig. 5A

Signal for both density and viscosity

DOWNHOLE SENSOR FOR FORMATION FLUID PROPERTY MEASUREMENT

CROSS-REFERENCE TO RELATED APPLICATION

The present application is a U.S. National Stage Application of International Application No. PCT/US2014/063168 filed Oct. 30, 2014, which is incorporated herein by reference in its entirety for all purposes.

BACKGROUND

The present disclosure relates to downhole sensors for detecting fluid properties in a hydrocarbon producing well. More particularly, the present disclosure relates to downhole sensor package for in-situ measuring thermophysical properties such as viscosity and/or density of downhole formation fluids.

Hydrocarbon producing wells may contain many different formation fluids (oil, water, and gas), and multi-phase mixtures, such as mixtures of water, gaseous hydrocarbons and fluidic hydrocarbons, each having different thermophysical properties. In order to evaluate the commercial value of a hydrocarbon producing well, it is useful to obtain information by understanding and analyzing the thermophysical properties of the formation fluid of the hydrocarbon producing well.

Thermophysical properties of formation fluid(s) present in a hydrocarbon producing well are typically obtained using downhole tools, such as wireline tools and logging while drilling (LWD) tools, as well as any other tool capable of being used in a downhole environment. In wireline measurements, a downhole tool, or logging tool, can be lowered into an open wellbore via a wireline. Once lowered to the depth of interest the measurements can be taken. LWD tools take measurements in much the same way as measurement while drilling (MWD) wireline-logging tools, except that the measurements are typically taken by a self-contained tool near the bottom of the bottomhole assembly and are recorded downward, as the well is deepened, rather than upward from the bottom of the hole as wireline logs are recorded.

One of the important thermophysical properties of formation fluid is its density. The density of a formation fluid can help identify the type of fluid (gas, oil or water) present in the formation. Another important thermophysical property of formation fluid is its viscosity, which may directly affect the producibility and the economic viability of a well. Typically, density is measured by using a density sensor located on a downhole tool, such as a wireline tool or LWD tool, and fluid viscosity is typically obtained from a separate viscosity sensor. It is desirable to directly measure and determine simultaneously both density and viscosity of formation fluids with a single downhole sensor package.

BRIEF DESCRIPTION OF THE DRAWINGS

These drawings illustrate certain aspects of some of the embodiments of the present disclosure, and should not be used to limit or define the disclosure.

While embodiments of this disclosure have been depicted and described and are defined by reference to example embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

The present disclosure relates to downhole sensors for detecting fluid properties in a hydrocarbon producing well. More particularly, the present disclosure relates to downhole sensor package for in-situ measuring thermophysical properties such as viscosity and/or density of downhole formation fluids.

Illustrative embodiments of the present disclosure are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the invention. Embodiments of the present disclosure may be applicable to horizontal, vertical, deviated, or otherwise nonlinear wellbores in any type of subterranean formation. Embodiments may be applicable to injection wells as well as production wells, including hydrocarbon wells. Embodiments may be implemented using a tool that is made suitable for testing, retrieval and sampling along sections of the formation. Embodiments may be implemented with tools that, for example, may be conveyed through a flow passage in tubular string or using a wireline, slickline, coiled tubing, downhole robot or the like. "Measurement-while-drilling" ("MWD") is the term generally used for measuring conditions downhole concerning the movement and location of the drilling assembly while the drilling continues. "Logging-while-drilling" ("LWD") is the term generally used for similar techniques that concentrate more on formation parameter measurement. Devices and methods in accordance with certain embodiments may be used in one or more of wireline (including wireline, slickline, and coiled tubing), downhole robot, MWD, and LWD operations.

A downhole sensor package is disclosed for measuring fluid density and/or viscosity in a downhole environment, and methods of using the same. In certain embodiments, the downhole sensor package may be an electromagnetic mechanical driven tubing vibration sensor package. In certain embodiments, the downhole sensor package may enable measurements of both fluid density and viscosity. In certain embodiments, the downhole sensor package may measure density and viscosity properties simultaneously. The sensor package may allow a viscosity sensing range of from about 0.1 cP to about 15,000 cP. In addition, the sensor package may allow a density sensing range of from about 0.03 g/cm$^3$ to about 2 g/cm$^3$. The sensor package may enable detection of kinematic viscosity, dynamic viscosity, and/or fluid density during various operations, such as openhole logging service. The downhole sensor package may further comprise at least one temperature and/or pressure sensor.

The downhole sensor package may comprise a fluid velocity controller to regulate the flow rate through the downhole sensor package. In certain embodiments, the fluid velocity controller may maintain the flow rate to a range of about 30 L/min to about 100 L/min. In certain embodiments, the downhole sensor package may be installed within an oil production well temporarily (for example, for about one day to about one year) and/or for an extended period of time (for example, installed permanently for the life of the oil production well), which may provide greater information of downhole conditions from a production well.

Figure 1:
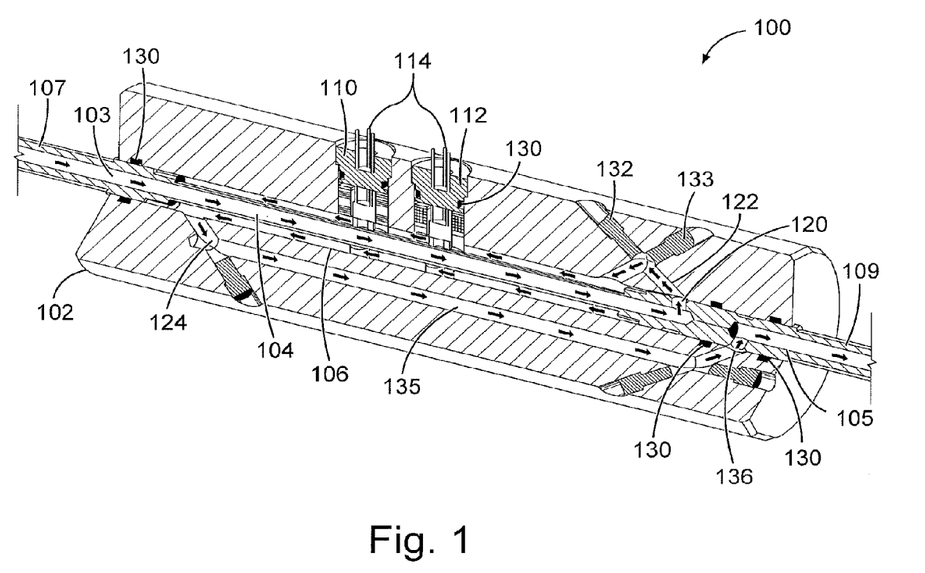
FIG. 1 is a cut-out side-view of a downhole sensor package, according to certain embodiments of the present disclosure.

Referring now to FIG. 1, a cutout view of a downhole sensor package 100 is shown according to embodiments of the present disclosure. The downhole sensor package 100 may comprise a housing 102, an inner flow tube 104, an outer flow annulus 106. The housing 102 may surround and protect the inner flow tube 104 and the outer flow annulus 106. A housing interior may be encapsulated within the housing 102, wherein the inner flow tube 104 and the outer flow annulus 106 may be located within the interior of the housing 102. The outer flow annulus 106 may be defined between the inner flow tube 104 and the housing 102.

The housing 102 may comprise a housing inlet port 103 and a housing outlet port 105. Fluid may be supplied to the inner flow tube 104 through a housing inlet port 103 and fluid may exit through the housing outlet port 105. In certain embodiments, the housing inlet port 103 and the housing outlet port 105 may be substantially axially aligned. In certain embodiments, the housing inlet port 103 and the housing outlet port 105 may be substantially axially aligned with the housing 102. In certain embodiments, a fluid supply tube 107 may be connected to the housing inlet port 103 to direct fluid towards the housing inlet port 103. In certain embodiments, a fluid discharge tube 109 may be connected to the housing outlet port 105 to direct fluid away from the housing outlet port 105.

The inner flow tube 104 may extend axially through the housing 102. The inner flow tube 104 may be connected to the outer flow annulus 106 to allow fluid communication between the inner flow tube 104 and the outer flow annulus 106. For example, in certain embodiments, fluid may flow from the inner flow tube 104 to the outer flow annulus 106 via a lower outlet port 120 and a first redirection path 122. Once fluid flows through the inner flow tube 104, the lower outlet port 120 may direct the fluid to the first redirection path 122, which may direct the fluid into the outer flow annulus 106. The first redirection path 122 may comprise gun-drilled lines in the housing 102. Seals 132, 133 may separate the fluid in the redirection path 122 from fluid outside the housing 102.

Once the fluid flows through the outer flow annulus 106, a second redirection path 124 may direct the fluid toward an auxiliary flow path 135 defined within the housing 102. The fluid may flow through the auxiliary flow path 135 toward a lower inlet 136. The fluid may flow through the lower inlet 136 and directed toward the housing outlet port 105.

In certain embodiments, the housing 102 may be made from a material in a configuration that may withstand pressures of at least 20,000 psi (pounds per square inch) at temperatures of at least 350° F. without substantial mechanical deformation of the housing. For example, in certain embodiments, the housing 102 may be comprised of Titanium and/or Hstaloy-HA276C. In another embodiment the housing 102 may be comprised of Titanium-alloy. In certain embodiments, the inner flow tube 104 may be made from the same material as the housing 102. The housing 102 may be comprised of a single body. In certain embodiments, the housing 102 may be formed using a molding process.

Figure 2:
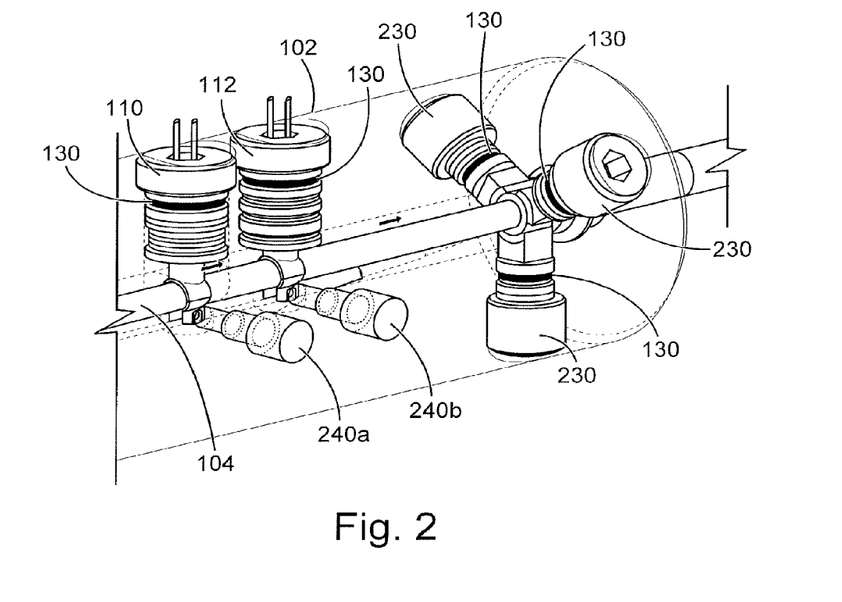
FIG. 2 is a side view of an end of the downhole sensor package with vibrating tube clamps and sensor vibration driving and pickup magnets and coils, according to certain embodiments of the present disclosure.

Referring now to FIG. 2, in certain embodiments, a plurality of tube clamp plugs 230 disposed in the housing 102 may engage the inner flow tube 104 and hold the inner flow tube 104 in place within the housing 102. For example, three tube clamp plugs 230 may be placed near each end of the housing 102, evenly spaced (about 120 degrees) apart. By clamping the inner flow tube 104 with tube clamp plugs 230 at each end, a clearly defined boundary condition for calculations may be provided. In certain embodiments, a torque meter may be used to maintain a constant mechanical strain on the clamping points during the package process.

In certain embodiments, the housing interior may be sealed from fluids outside the housing 102. As such, an internal housing pressure may be generated within the housing interior. In certain embodiments, a piston or electric pump may be connected to the fluid supply tube from a formation sampling process line for fluid rate control. For example, the piston or electric pump may direct fluid through the fluid supply tube at a flow rate of about 30 L/min to about 100 L/min.

In certain embodiments, the downhole sensor package may further comprise at least one temperature and/or pressure sensor. For example, at least one temperature sensor may be configured to detect temperature of fluid within the inner flow tube 104 and/or temperature of fluid within the outer flow annulus 106. For example, at least one pressure sensor may be configured to detect pressure of fluid within the inner flow tube 104 and/or pressure of fluid within the outer flow annulus 106.

Referring to FIGS. 1 and 2, the outer flow annulus 106 and secondary flow path 135 within the housing 102 may be sealed from fluid outside the housing 102. For example, a plurality of O-rings 130 may be located on the vibrating tube 104, the tube clamp plugs 230, and on the vibration source 110 and vibration detector 112 to separate the fluid inside the housing 102 from fluid outside the housing 102.

The downhole sensor package 100 may comprise a vibration source 110 and a vibration detector 112. A measurement module 114 may be connected to the vibration source 110 to control tubing vibration generation and the vibration detector 112 to read tubing displacement data. The vibration source 110 and the vibration detector 112 may engage the inner flow tube 104. The vibration source 110 and vibration detector 112 may be located side by side as shown in FIG. 1. Other source/detector configurations may also be used. The vibration source 110 can include any means capable of exciting the inner flow tube 104 into one or more of its resonance modes as recognized by one of ordinary skill in the art with the benefit of this disclosure. In certain embodiments, the vibration source 110 may comprise one or more magnet and/or coil assemblies. The vibration detector 112 may include any means capable of detecting a corresponding vibration of the inner flow tube 104 as recognized by one of ordinary skill in the art with the benefit of this disclosure. For example, the vibration detector 112 may comprise one or more magnet and/or coil assemblies. In another embodiment, the vibration detector 112 may be comprised of a capacitance based sensor. In a further embodiment, an eddy current sensor may be used for tubing displacement detection.

In certain embodiments, the inner flow tube 104 may have an inner flow pressure and the outer flow annulus 106 may have an outer flow pressure. In certain embodiments, the inner flow pressure and the outer flow annulus may be substantially the same. For example, the inner flow pressure and the outer flow pressure may be substantially equalized by being in fluid communication through the lower outlet port 120. As a result, the inner flow tube 104 may not need to withstand strong pressure differences and may allow for a thin inner flow tube wall, and reduction of the mass of the inner flow tube. Equalization of pressure across the inner flow tube 104 may allow a broader range of materials to be used for the inner flow tube 104. For example, the flow tube 104 may be comprised of titanium and/or titanium alloy. In addition, a smaller magnet may be used in the vibration source 110 to achieve the vibration amplitude.

Figure 3:
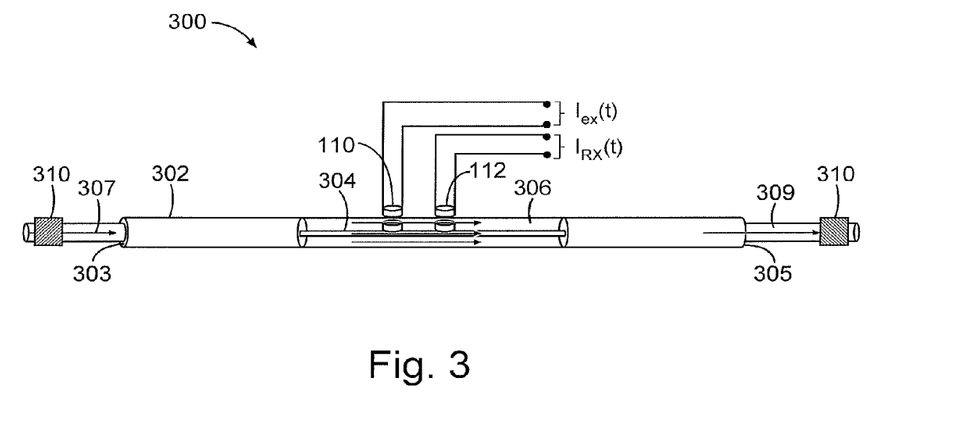
FIG. 3 is a schematic view of the downhole sensor package and fluid flowing line connection, according to certain embodiments of the present disclosure.

Referring now to FIG. 3, another embodiment of the downhole sensor package 300 is shown for installing into a downhole logging tool, comprising a housing 302, an inner flow tube 304, and an outer flow annulus 306. The outer flow annulus 306 may be defined in an annulus between the inner flow tube 304 and the housing 302. Fluid flowing into a fluid input port 303 may be diverted to either the inner flow tube 304 or the outer flow annulus 306 by a flow diverter. For example, in certain embodiments, a 45° flow tube may be used to direct flow of fluid from the inner flow tube 304 to the outer flow annulus 306, and exit from the fluid output port 305. This flow circulation enables vibration of the inner flow tube 304 with maximum interaction area with fluid in the outer flow annulus 306, enhancing a fluid friction induced damping effect that may enhance the vibration amplitude decay rate of the inner flow tube.

Figure 4:
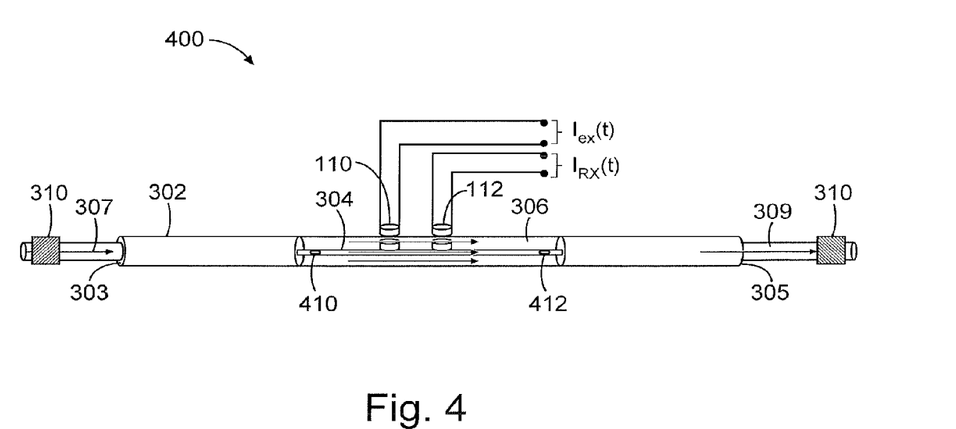
FIG. 4 is a schematic view of the another embodiment of the downhole sensor package with holes for fluid flowing through the tube and cavity, according to certain embodiments of the present disclosure.

Referring now to FIG. 4, another embodiment of the downhole sensor package 400 is shown comprising a housing 302, an inner flow tube 304, an outer flow annulus 306, and holes 410, 412 in the inner flow tube 304. In certain embodiments, a first hole 410 may be located at an upper end of the inner flow tube 304. In certain embodiments, a second hole 412 may be located at a lower end of the inner flow tube 304. The first hole 410 and/or the second hole 412 may allow fluid communication between the inner flow tube 304 and the outer flow annulus 306. As such, the pressure between the inner flow tube 304 and the outer flow annulus 306 may be substantially equal. In addition, in certain embodiments, the diameter ($\phi$) of the holes may be substantially less than the diameter ($\Phi$) of the inner flow tube so that $\phi/\Phi \ll 1$. For example, in one embodiment, the ratio of hole diameter $\phi$ to inner flow tube diameter $\Phi$ may be less than 0.1. In another embodiment, this ratio may be range between about 0.01 and 0.1.

Figure 5A:
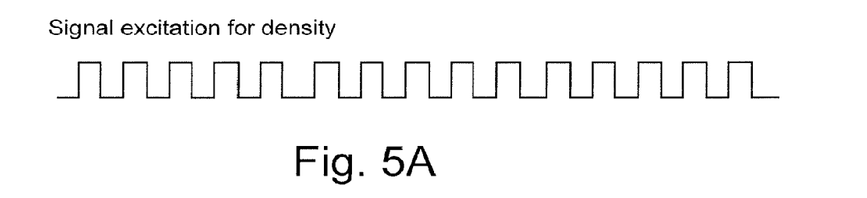
FIG. 5A is a diagram of a time-modulated constant-amplitude driving signal for density measurement, according to certain embodiments of the present disclosure.

In certain embodiments, the vibration source 110 may be modulated to enable the downhole sensor package 100 to operate in a density detection mode or in viscosity detection mode. During the density detection mode, the downhole sensor package 100 may measure the density of fluid flowing through the downhole sensor package 100. Referring to FIG. 5A, an example driving signal for detecting density is shown. The driving signal may be characterized by its time-modulated constant-amplitude for continuing excitation on the tubing vibration. In certain embodiments, the driving signal may have a frequency chosen with regard to the intrinsic frequency of the inner flow tube. For example, in certain embodiments, the driving signal may be within about 2000 Hz of the intrinsic frequency of the inner flow tube.

Figure 5B:
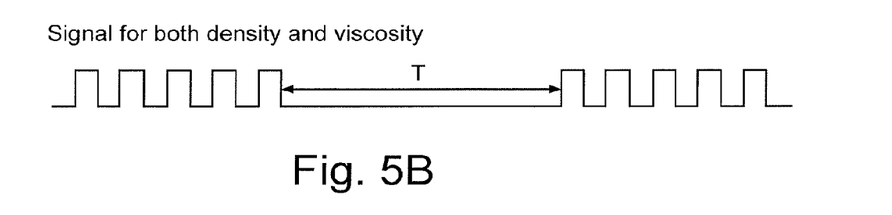
FIG. 5B is a diagram of a combined time-modulated and amplitude-modulated driving signal for simultaneously measuring density and viscosity properties, according to certain embodiments of the present disclosure.

During the viscosity detection mode, the downhole sensor package may measure the viscosity of fluid flowing through the downhole sensor package. Referring to FIG. 5B, an example driving signal for detecting viscosity is shown, where the driving signal is delayed for a period of time (t) to allow measurement of fluid damping on the inner flow tube.

Figure 6:
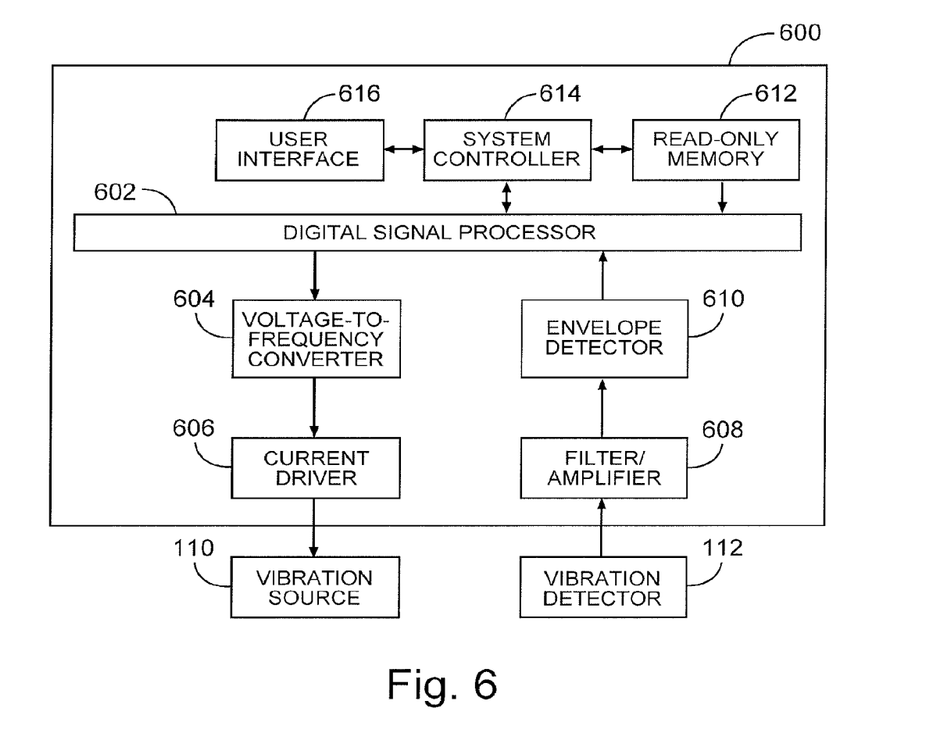
FIG. 6 is a diagram showing a measurement module design, according to certain embodiments of the present disclosure.

Referring now to FIG. 6, an embodiment of the signal processing module may include a processor 602, e.g. a digital signal processor, voltage-to-frequency converter 604, a current driver 606, a filter/amplifier 608, an amplitude detector 610, and a read-only memory (ROM) 612. The processor 602 may be configured and controlled by a system controller 614 that operates in response to actions of the user on the user interface 616. The system controller 614 may also retrieve measurements from the processor 602 and provides them to the user interface 616 for display to a user.

The processor 602 may execute a set of software instructions stored in ROM 612. The processor 602 may include digital to analog (D/A) and analog to digital (D/A) conversion circuitry for providing and receiving analog signals to off-chip components. In performing one of the methods described further below, the processor 602 may provide a voltage signal to the voltage-to-frequency converter 604. The voltage-to-frequency converter 604 may produce a driving signal having a frequency proportional to the input voltage. The current driver 606 may receive this frequency signal, amplify it, and send an amplified driving signal to the vibration source 110. In response, the vibration source 110 may apply a corresponding periodic force on the inner flow tube, causing the inner flow tube to vibrate. In certain embodiments, the driving signal may have an amplitude sufficient to excite the inner flow tube vibrating at its natural vibration frequency, as would be recognized by one of ordinary skill in the art with the benefit of the present disclosure. The resulting vibration of the inner flow tube may be detected by the vibration detector (comprised of a second set of magnet and/or coil assembly) to generate a tubing displacement signal. The vibration detector 112 may send the tubing displacement signal to the measurement module 600. A filter/amplifier 608 may receive the detection signal from vibration detector 112 and provide some filtering and amplification of the detection signal before passing the detection signal to the amplitude detector 610. The filter/amplifier 608 serves to isolate the vibration detector 112 from the amplitude detector 610 to prevent the amplitude detector 610 from electrically loading the vibration detector 112 and thereby adversely affecting the detection sensitivity. The amplitude detector 610 may produce a voltage signal indicative of the amplitude of the detection signal. The processor 602 may measure this voltage signal, and may thereby be able to determine the vibration amplitude for the chosen vibration frequency.

The measurement module 600 may employ the vibration source 110 and the vibration detector 112 to locate and characterize the resonance frequencies of the inner flow tube. Several methods are contemplated and non-limiting examples are given herein. In a first method, the measurement module 600 may cause the vibration source 110 to perform a frequency sweep across the range of interest, and record the amplitude readings from the vibration detector 112 as a function of the frequency. A plot of the vibration amplitude versus frequency may show a peak at the resonance frequency $f_0$. The resonance frequency can be converted to a density measurement, and the linewidth of the peak may yield additional information such as viscosity. In the second method, the measurement module 600 may excite the inner flow tube at a specific frequency, such as the tube natural frequency, but with different amplitudes. A plot of the vibration amplitude of the inner flow tube versus exciting amplitude may show an optimum exciting amplitude for exciting tubing vibration at its resonance frequency $f_0$. The resonance amplitude decay of the inner flow tube may be converted to a fluid viscosity property measurement, and the linewidth, $\Delta f$, of the resonant peak may yield additional information, such as system quality factor ($Q=f_0/\Delta f$) information.

The measurement module 600 may also or alternatively track the resonance frequency using a feedback control technique. An initial step size for changing the frequency may be chosen, which can be positive or negative to respectively increase or decrease the frequency. The vibration source may then be activated and an initial amplitude measurement may be made. The vibration frequency may then be adjusted by the step size and another measurement of the amplitude may be made at the new frequency. These measurements may be compared and an estimate of the derivative may be made. From this estimated derivative, a distance and direction to the resonance peak can be estimated. The estimated distance and direction information may be used to adjust the step size and the processor may repeat the sequence. This method may allow fast measurement response to changing fluid densities.

In certain embodiments, the measurement module may process the detection signal in the time-domain and/or frequency-domain in-situ for field test real-time report. The signal detected and/or generated by the vibration detector may then be analyzed to determine properties of the fluid flowing through the downhole sensor package.

In another method, the measurement module 600 may employ an iterative technique to search for the maximum amplitude as the frequency is discretely varied. Any known algorithm for finding minima or maxima may be used. For example, the search method may use a back-and-forth search method in which the measurement module 600 may sweep the vibration source frequency from one half-amplitude point across the peak to the other half-amplitude point and back again. For example, the vibration may be induced at an initial (minimum) frequency and the vibration amplitude may be measured and set as a threshold. The frequency may then be increased by a predetermined amount and the amplitude at the new frequency may be measured. The measured amplitude may then be compared to the threshold amplitude, and if larger, then the threshold is set to be equal to the measured amplitude. This may be repeated until the measured amplitude falls below the threshold. At this point, the threshold may indicate the maximum measured amplitude, which occurred at the resonance peak. The frequency may then continue to be increased and corresponding amplitude compared to half the resonance frequency, until the amplitude measurement falls below half of the resonance frequency. This may also be repeated in the opposite direction, from high frequency to low frequency across the resonant frequency. From this data, the peak width and asymmetry may be determined, and fluid density, viscosity, and multiple phase information be calculated.

The combined time-modulated and amplitude-modulated functions and/or processing modes may enable simultaneous measurement on both density and viscosity. In certain embodiments, for measuring the density of downhole fluids, the driving signal may be only time-modulated with a constant-excitation amplitude. For measuring the viscosity, the driving signal may be amplitude modulated from a pre-set amplitude A(0) to an amplitude of zero.

The viscosity of fluid flowing through the outer flow annulus may be measured by the downhole sensor package. In certain embodiments, the vibration source may cease to apply the driving force to the inner flow tube for a viscosity measurement time period. In certain embodiments, the viscosity measurement time period may be about 10 ms to about 5 sec. While the driving signal is paused, the vibration detector may output the measured displacement of the inner flow tube over time for amplitude decay characteristic analysis. During the viscosity measurement time period, vibration of the inner flow tube may be dampened by fluid flowing through both the outer flow annulus and the inner flow tube, as shown by the example displacement amplitude (dBV) vs. Time graph shown in FIG. 7A. In certain embodiments, the amplitude decay may be described by $A_t = A_0^{-\alpha t}$, where $A_0$ is the initial vibration amplitude, and $\alpha$ is sensor's decay coefficient. The fluid in the outer flow annulus may increase the damping factor proportional to $\gamma = 2 + (OD-ID)/ID$, where OD is the outer diameter of the inner flow tube and ID is the inner diameter of the inner flow tube.

Assuming the damping force is proportional to fluid velocity ($\delta^2 \psi / \delta^2 t$), a motion equation of the inner flow tube when vibrating in the flowing fluid may be expressed by:

$$\frac{d^2\psi}{d^2 t} + \frac{k}{m}\psi + \frac{(\eta_1 + \eta_2)}{m}\frac{d\psi}{dt} = 0$$

where $\eta_1$ and $\eta_2$ represent damping contributions from fluid flowing in the inner flow tube and the outer flow annulus, respectively. The effective damping parameter can be described by:

$$\eta_{\mathit{eff}} = (\eta_1 + \eta_2) \approx \eta\left(2 + \frac{OD - ID}{ID}\right)$$

Under small-damping conditions, the inner flow tube resonant frequency can be found as:

$$f = \sqrt{f_0^2 + \left(\frac{\eta_{\mathit{eff}}}{4\pi m}\right)^2}$$

where $f_0$ represents hollow tube vibrating resonant frequency under vacuum conditions. And the corresponding linewidth of the resonant peak is:

$$\Delta f = \frac{\eta_{\mathit{eff}}}{2\pi m}$$

From this, a quality factor may be described by the following equation:

$$q = \frac{f}{\Delta f} = \sqrt{f_0^2 + \left(\frac{\eta_{\mathit{eff}}}{4\pi m}\right)^2} * \frac{2\pi m}{\eta_{\mathit{eff}}}$$

Thus, when density is available, the kinematic viscosity may be found as:

$$v = \frac{\eta_{\mathit{eff}}}{\rho} \approx v_0 + A(T, P) * \frac{\eta_{\mathit{fluid}}}{\rho_{\mathit{fluid}}}$$

where $v_0$ represents a sensor package intrinsic property that may be determined by sensor material and package geometry, and A(T, P) may be a calibration factor as compared to a standard fluid.

For downhole fluid analysis under high-temperature and pressure conditions, both linewidth of the resonant frequency peak and system quality factor may be a function of the temperature and pressure. In one example, the linewidth of the resonant peak may be expressed as:

$$Ln(\eta) = A + B * \Delta f$$

where viscosity is a function of linewidth. For a specific fluid, the linewidth will depend upon temperature.

Figure 7A:
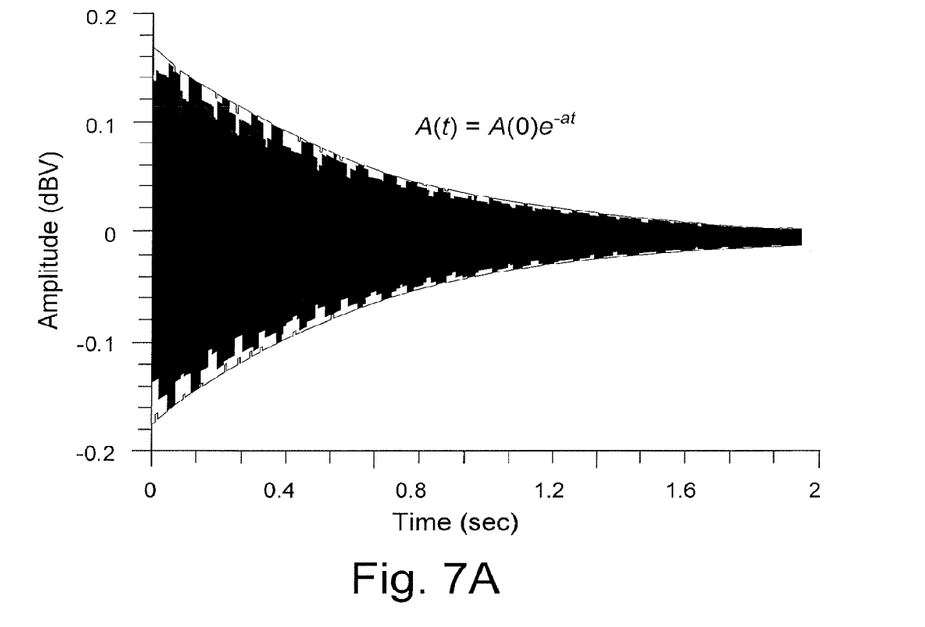
FIG. 7A is an example plot of the inner flow tube vibration amplitude versus time during dampening measured during signal driving as shown by example in FIG. 5B, according to certain embodiments of the present disclosure.
Figure 7B:
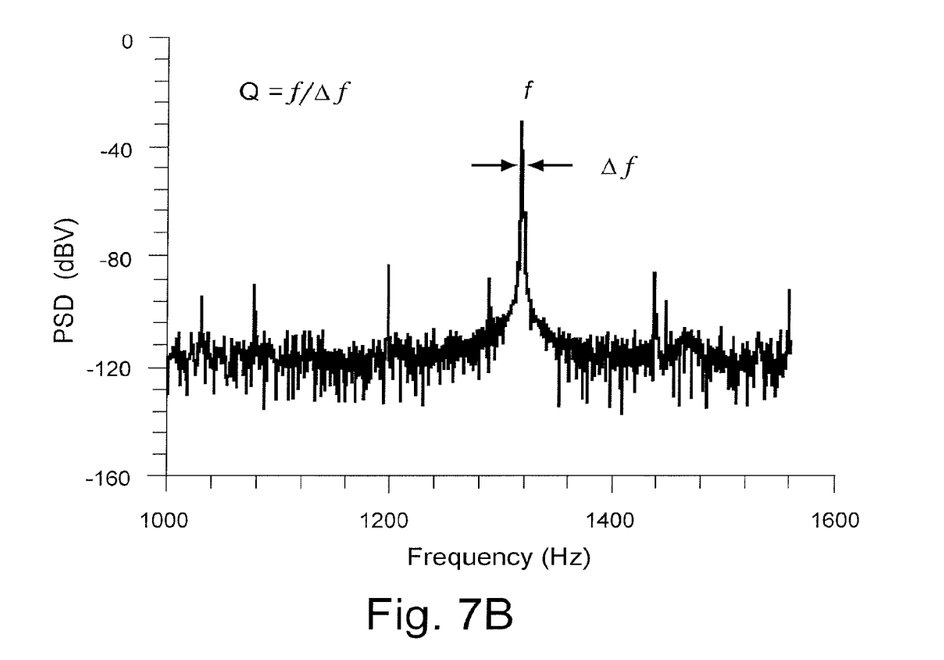
FIG. 7B is an example plot of the viscosity determination from linewidth of the frequency peak of the power spectral density, according to certain embodiments of the present disclosure.

Referring now to FIGS. 7A and 7B, example plots of the vibrating inner flow tube are shown under light damping conditions. FIG. 7A shows attenuation of the vibration amplitude over time. FIG. 7B shows the corresponding power spectral density (PSD) of the inner flow tube, obtained by using a fast Fourier transform. The PSD plot shows the resulting resonant frequency (f) under a fluid flowing condition, and the linewidth (Δf) of the frequency peak at 3 dB. Determination of the viscosity may be based on the linewidth measured from the resonant peak at its resonant frequency.

Figure 8:
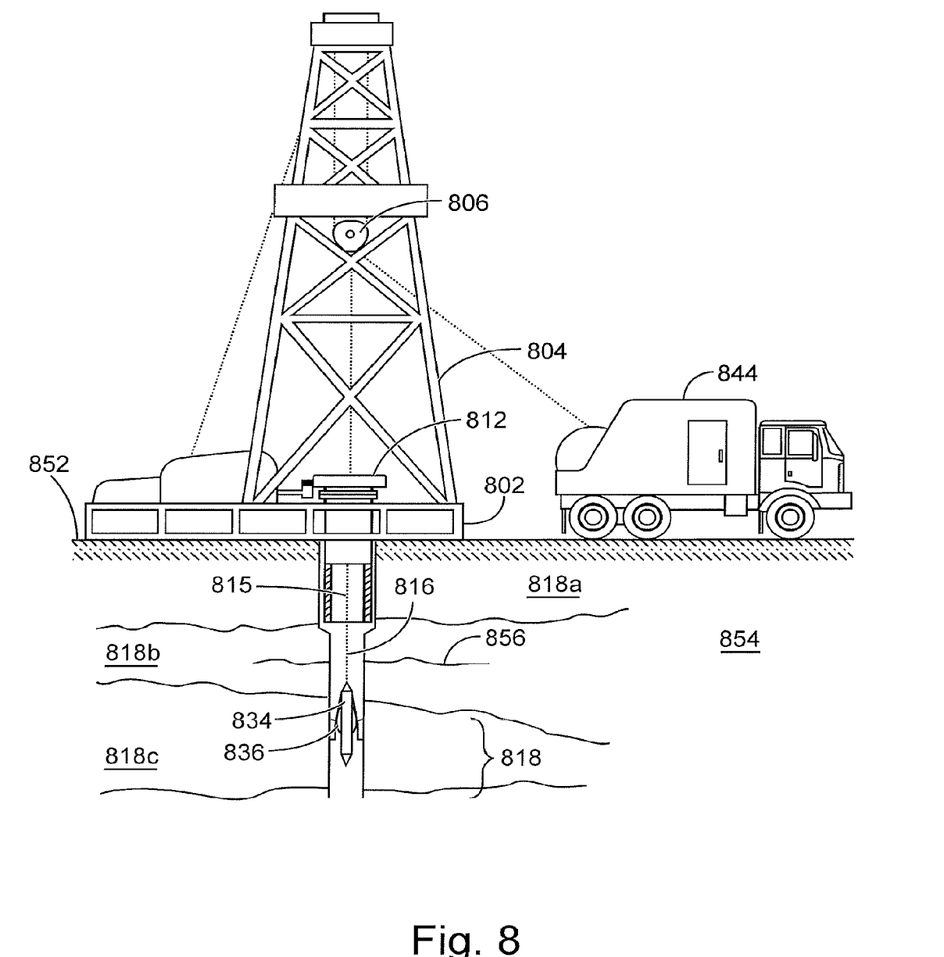
FIG. 8 is a diagram showing an illustrative wireline logging environment, according to aspects of the present disclosure.

FIG. 8 is a diagram of a subterranean drilling system, according to aspects of the present disclosure. The drilling system comprises a drilling platform 802 positioned at the surface 852. In the embodiment shown, the surface 852 comprises the top of a formation 854 containing one or more rock strata or layers 818a-c, and the drilling platform 802 may be in contact with the surface 852. In other embodiments, such as in an off-shore drilling operation, the surface 852 may be separated from the drilling platform 802 by a volume of water.

Measurement/logging operations can be conducted using a wireline tool 834, i.e., an instrument that is suspended into the borehole 816 by a cable 815 having conductors for transporting power to the tool and telemetry from the tool body to the surface 852. The drilling system may comprise a derrick 804 supported by the drilling platform 802 and having a traveling block 806 for raising and lowering the wireline tool 834.

The wireline tool 834 may comprise a downhole sensor package 836. The downhole sensor package 836 may comprise a plurality of transmitters and receivers (e.g., antennas capable of receiving and/or transmitting one or more electromagnetic signals) such as magnetic dipoles that are axially spaced along the length of the tool and positioned at different angles with respect to the tool 836.

The downhole sensor package 836 may be communicatively coupled to the cable 815. A facility 844 (shown in FIG. 8 as a truck, although it may be any other structure) may collect measurements from the downhole sensor package 836, and may include computing facilities (including, e.g., an information handling system) for controlling, processing, storing, and/or visualizing the measurements gathered by the downhole sensor package 836. The computing facilities may be communicatively coupled to the downhole sensor package 836 by way of the cable 815. In certain embodiments, the information handling system 832 may serve as the computing facilities of the logging facility 844. In certain embodiments, some or all of the measurements taken at the downhole sensor package 836 may also be stored within the tool 836 for later retrieval at the surface 852.

As described above, FIG. 8 shows a formation 854 one or more rock strata or layers 818a-c. Each of the strata 818a-c shown in FIG. 8 may have different physical and electrical characteristics. For example, some of the strata may be generally conductive while others may be generally resistive. Likewise, some may be generally porous while some may be non-porous. In certain instances, natural fractures or cracks may be located within strata 818a-c. In FIG. 8, the borehole 816 intersects a fracture 856 in layer 818b. Fracture 856 may have different characteristics than the rock layer in which it is located, and the different characteristics may skew the measurements of the strata. For example, layer 818b may comprise a resistive layer, yet fracture 856 may contain conductive fluids, or layer 818b may comprise a conductive layer, yet fracture 856 may contain resistive fluids. Identifying, characterizing, and accounting for these fractures may, therefore, improve the resulting measurements of the formation 854 generally and the strata 818a-c in particular.

In certain embodiments, a method for using the downhole sensor package to detect one or more properties of a downhole fluid may comprise receiving the downhole fluid into an inner flow tube, located within a sensor housing; directing the downhole fluid to an outer flow annulus defined between the sensor housing and the inner flow tube; displacing the inner flow tube at an excitation frequency with a periodic displacement signal generated by a vibration source during a density measurement period; detecting an inner flow tube density displacement during the density measurement period; removing the periodic displacement signal generated by the vibration source during a viscosity measurement period; detecting an inner flow tube viscosity displacement during the viscosity measurement period; sending the inner flow tube density displacement or the inner flow tube viscosity displacement to a system controller; adjusting one or more operation conditions in response to the density or viscosity of the downhole fluid.

In certain embodiments, a method for determining density and viscosity of a formation fluid may comprise receiving a fluid into an inner flow tube, located within a sensor housing; directing the fluid to an outer flow annulus defined between the sensor housing and the inner flow tube; determining a resonant frequency, linewidth, or Q value of the tube containing the fluid; calculating the density of the fluid using the resonant frequency; calculating the viscosity of the fluid using the linewidth value of the resonant frequency peak; and adjusting downhole well conditions in response to the density of the fluid.

As such, vibration data supplied by the downhole sensor package may be analyzed by the system controller and may signal a changed in downhole fluid conditions. In response to vibration data signaling changed downhole fluid conditions, an operator may adjust operation parameters, and/or take steps to adjust downhole conditions, as would be appreciated to one of ordinary skill in the art with the benefit of the present disclosure. Accordingly, the downhole sensor package may provide the operator information concerning thermophysical properties of downhole fluids, which the operator may use to make operational decisions.

EXAMPLE

Figure 9:
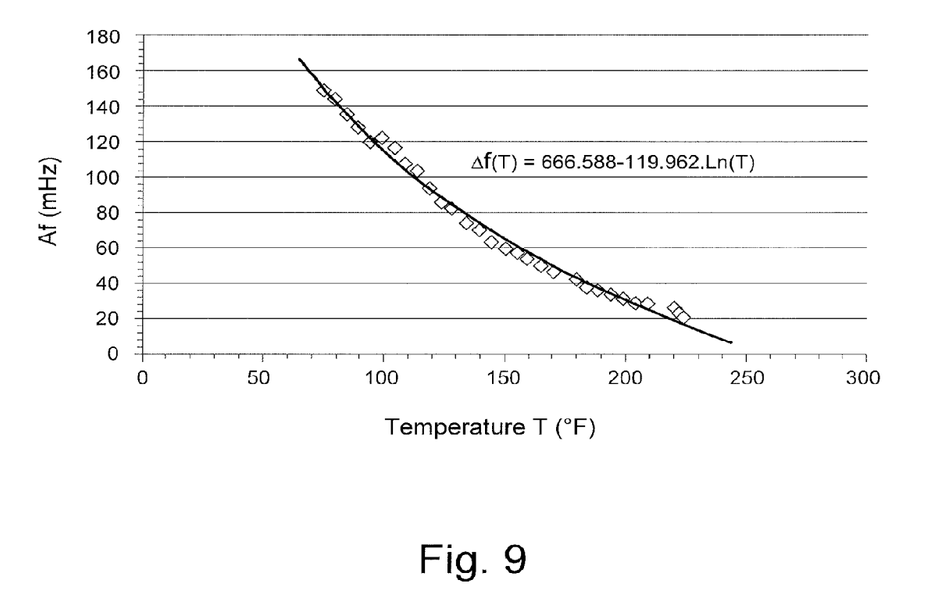
FIG. 9 is an example plot of linewidth with respect to temperature for an example downhole oil mixture, according to certain embodiments of the present disclosure.

As an example of linewidth over a range of temperatures for an example downhole mineral oil fluid as may be measured by the downhole sensor package is shown in FIG. 9. A hydrocarbon fluid sample is circulated into the downhole sensor package as shown in FIG. 1 with a circulation pump, while the downhole sensor package is kept in an isothermal test rig. The linewidth, given by $\Delta f(T)$, variations with respect to temperature (T) may be expressed as $\Delta f(T) = 666.588 - 119.926 \cdot Ln(T)$. In addition, the viscosity ($\eta$) of this fluid may be expressed as $Ln(\eta) = 22.005 - 3.351 \cdot Ln(T)$, which was measured by standard viscometer instrument. As such, the correlation between linewidth $\Delta f(T)$ and viscosity $\eta$ is represented by $Ln(\eta) = A + B \cdot \Delta f$, with $A = (c - d \cdot a/b)$ and $B = d/b$, where $\Delta f(T) = a + b \cdot Ln(T)$ and $Ln(\eta) = c + d \cdot Ln(T)$. In general, the logarithm scale viscosity may be proportional to linewidth of the resonant peak that can be directly measured from decay data.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. The indefinite articles "a" or "an," as used in the claims, are defined herein to mean one or more than one of the element that it introduces.

What is claimed is:

1. A downhole sensor package system comprising: a sensor housing having a fluid input port and a fluid output port;
    an inner flow tube located within and axially defined with the sensor housing; an outer flow annulus defined between the inner flow tube and the sensor housing, wherein the inner flow tube is in fluid communication with the outer flow annulus to enable fluid flow from the inner flow tube to the outer flow annulus; and
    a vibration source and a vibration detector engaging the inner flow tube, wherein the vibration source displaces the inner flow tube for a density measurement time period, and wherein displacement of the inner flow tube is delayed with the vibration source for a viscosity measurement time period.

2. The system of claim 1, wherein the vibration source comprises one or more magnets and coils configured to displace the inner flow tube.

3. The system of claim 1, wherein the vibration detector comprises one or more magnets and coils configured to detect displacement of the inner flow tube.

4. The system of claim 1, wherein the vibration source and vibration detector are vertically aligned.

5. The system of claim 1, further comprising a signal processing module connected to the vibration detector.

6. The system of claim 1, further comprising at least one tube clamp engaging an upper end of the inner flow tube and a lower end of the inner flow tube.

7. The system of claim 1, wherein the housing can withstand a pressure difference of up to about 20,000 psi.

8. The system of claim 1, wherein the pressure within the inner flow tube is lower than the formation pressure within a downhole tool flowline.

9. The system of claim 1, wherein the inner flow tube is made from Titanium or Titanium-alloy.

10. A method for determining density and viscosity of a formation fluid, comprising:
    receiving a fluid into an inner flow tube, the inner flow tube disposed within a sensor housing;
    directing the fluid from the inner flow tube to an outer flow annulus defined between the sensor housing and the inner flow tube;
    displacing the inner flow tube with a vibration source for a density measurement time period;
    determining a resonant frequency, linewidth, and Q value of the tube containing the fluid;
    calculating the density of the fluid using the resonant frequency;
    calculating the viscosity of the fluid using the linewidth value of the resonant frequency peak;
    delaying displacement of the inner flow tube with the vibration source for a viscosity measurement time period; and
    adjusting downhole well conditions in response to the density of the fluid.

11. The method of claim 10, wherein calculating the viscosity of the fluid comprises calculating the dynamic viscosity of the fluid using the density and linewidth value of the resonant frequency peak.

12. The method of claim 10, wherein displacing the inner flow tube with a vibration source is at a modulated frequency.

13. The method of claim 12, wherein displacing the inner flow tube further comprises displacing downhole fluid through the inner flow tube at a flow rate from about 30 L/min to about 100 L/min.

14. The method of claim 12, further comprising detecting a density displacement of the inner flow tube with a vibration detector during the density measurement time period and sending the density displacement of the inner flow tube to a signal processing module.

15. The method of claim 12, further comprising:
detecting a viscosity-damped displacement of the inner flow tube with a vibration detector during the viscosity measurement time period; and
sending the viscosity-damped displacement to a signal processing module.

16. The method of claim 15, further comprising adjusting one or more downhole well conditions in response to the viscosity-damped displacement of the inner flow tube.

17. A method for detecting one or more properties of a downhole fluid, comprising:
receiving the downhole fluid into an inner flow tube disposed within a sensor housing;
directing the downhole fluid from the inner flow tube to an outer flow annulus defined
between the sensor housing and the inner flow tube;
displacing the inner flow tube at an excitation frequency with a periodic displacement signal generated by a vibration source during a density measurement period;
detecting an inner flow tube resonant frequency during the density measurement period;
delaying displacement of the inner flow tube generated by the vibration source during a viscosity measurement period;
detecting an inner flow tube viscosity-damped displacement during the viscosity measurement period;
sending the inner flow tube resonant frequency or the inner flow tube viscosity-damped displacement to a system controller; and
adjusting one or more operation conditions in response to the density or viscosity of the down hole fluid.

18. The method of claim 17, further comprising measuring temperature or pressure of the downhole fluid.

19. The method of claim 17, wherein the viscosity measurement period is about 10 ms to about 5 seconds in duration.

20. The method of claim 17, further comprising periodically alternating between the density measurement period and the viscosity measurement period.

* * * * *